US007987735B2

(12) United States Patent
Mann, III et al.

(10) Patent No.: US 7,987,735 B2
(45) Date of Patent: Aug. 2, 2011

(54) CORRELATING PUSH FORCE AND STALK VIBRATION TO A PLANT'S SUSCEPTIBILITY TO ROOT LODGING

(75) Inventors: Julian Adin Mann, III, Ames, IA (US); Ashli J. Armstrong, Dubuque, IA (US); Roberto Barreiro, Honolulu, HI (US); Christopher L. Baszczynski, Earlham, IA (US); Terry EuClaire Meyer, Urbandale, IA (US)

(73) Assignees: Iowa State University Research Foundation, Inc., Ames, IA (US); Pioneer Hi-Bred International, Inc., Johnston, IA (US)

( * ) Notice: Subject to any disclaimer, the term of this patent is extended or adjusted under 35 U.S.C. 154(b) by 75 days.

(21) Appl. No.: 12/577,329

(22) Filed: Oct. 12, 2009

(65) Prior Publication Data

US 2010/0089176 A1   Apr. 15, 2010

Related U.S. Application Data

(60) Provisional application No. 61/190,060, filed on Oct. 10, 2008.

(51) Int. Cl.
*G01L 1/10* (2006.01)
(52) U.S. Cl. ..................... 73/862.59; 73/760
(58) Field of Classification Search ............ 73/781–788, 73/862.59, 760
See application file for complete search history.

(56) References Cited

U.S. PATENT DOCUMENTS

| 4,328,641 | A | * | 5/1982 | Tesch ............................ 47/59 R |
|4,650,336|A|*|3/1987|Moll ............................. 356/417|
|5,044,210|A| |9/1991|Kuhn et al.|
|6,496,136|B1|*|12/2002|Mucciardi ...................... 342/22|
|6,983,582|B1| |1/2006|Muckler|
|7,412,880|B2|*|8/2008|Barreiro et al. ............ 73/170.07|
|2007/0125155|A1| |6/2007|Barreiro et al.|
|2007/0294994|A1| |12/2007|Deppermann et al.|
|2009/0188162|A1|*|7/2009|Bornemeier et al. ............. 47/42|
|2010/0026492|A1|*|2/2010|Grieco et al. ............. 340/572.1|
|2010/0089178|A1| |4/2010|Tragesser et al.|

FOREIGN PATENT DOCUMENTS

WO    WO 2007/149984 A2    12/2007

OTHER PUBLICATIONS

Cilas, Christian et al., "Variability in the Rigidity of Coffea Canephora Pierre Stems Determined by Acoustic Analysis", Trees (2002) 16:23-27.

(Continued)

*Primary Examiner* — Max Noori
(74) *Attorney, Agent, or Firm* — McKee, Voorhees & Sease, P.L.C.

(57) ABSTRACT

The present device enables measurement of the susceptibility of corn plants to root lodging. The device is used to push over a corn stalk and the force used to push over the stalk, and the vibration of the stalk caused by the push are recorded. As material breaks in the stalk, an accelerometer, measures stalk vibration response to the breaking events; the data is then recorded to allow quantitative measurements of the susceptibility of corn plants to root lodging. This allows meaningful comparisons of various hybrids at early stages of hybrid evaluation and advancement.

11 Claims, 5 Drawing Sheets

OTHER PUBLICATIONS

Fouere, Alain et al., "A Portable Electronic Device for Evaluating Root Lodging Resistance in Maize", http://agron.scijournals.org/cgi/content/abstract/87/5/1020, printed from Internet Feb. 3, 2010, 1 page.

Database Compendex, Van Canneyt T. et al., "The Effect of Preload, Frequency, Temperature and Internal Quality Parameters of Potato Tissue on Visco-Elastic Vibration Damping and Complex Modulus Properties", XP002564390. Data Accession No. E2005078839218 Abstract. 2 pages.

International Search Report, Iowa State University Research Foundation, Inc., PCT/US2009/060340 dated Jan. 29, 2010.

Fouere, Alain et al., "A Portable Electronic Device For Evaluating Root Lodging Resistance in Maize", Agronomy Journal, vol. 87, Sep.-Oct. 1995, pp. 1020-1024.

\* cited by examiner

CORRELATING PUSH FORCE AND STALK VIBRATION TO A PLANT'S SUSCEPTIBILITY TO ROOT LODGING

CROSS-REFERENCE TO RELATED APPLICATIONS

This application claims priority under 35 U.S.C. §119 to provisional application Ser. No. 61/190,060 filed Oct. 10, 2008, herein incorporated by reference in its entirety.

FIELD OF THE INVENTION

This invention relates to a method and device for measuring the susceptibility of corn plants to root lodging. The invention provides a way of measuring and recording root lodging so the data can be specifically used to provide meaningful information in hybrid corn breeding to facilitate the development of corn plants having good root lodging properties.

BACKGROUND OF THE INVENTION

Corn is an important and valuable field crop. Thus, a continuing goal of plant breeding is to develop stable, high yielding corn hybrids that are agronomically sound. The reasons for this goal are obvious: To maximize the amount of grain produced on the land and to supply food for both animals and humans.

The overall goal of a corn plant breeder is to combine, in a single variety/hybrid, various desirable traits of the parental lines. For field crops, these traits may include resistance to diseases and insects, tolerance to heat and drought, reducing time to crop maturity, greater yield, and better agronomic qualities. The mechanical harvesting of many crops has placed increased importance on the uniformity of plant characteristics such as germination, stand establishment, growth rate to maturity, and fruit size.

In order to have the plants stand tall and withstand the various mechanical forces applied by wind, rain, harvesting equipment, etc., it is important that the plant stalk have good mechanical properties and that the roots are firmly anchored into the soil. Otherwise, the stalks may bend, break or be pulled out, leading to the loss of a harvestable ear.

It has become common place for corn plant breeders to use a set of fairly standard definitions for characterization of the mechanical properties of roots and stalks. For example, brittle snap is a measure of the stalk breakage below the ear during ear development and is an indication of whether a hybrid will snap or break near the time of flowering, under severe winds. Data is often presented as a percentage of plants that do not snap after a wind event.

Stalk lodging, is a trait measured near harvest time, and is scored as the percentage of plants that do not exhibit stalk breakage at the base of the plant, when measured either by observation of natural lodging in the field, or by physically pushing on stalks, and then determining the percentage of plants that break or do not break at the base of the plant.

Root lodging is a trait scored as the percentage of plants in a plot or field that do not exhibit excess leaning of the plant from the normal vertical axis. Typically, plants that lean from the vertical axis at an approximately 30 degree angle or greater would be counted as lodged. Root lodging often is reported as a rating of one to nine where a higher score indicates less root lodging potential (one is very poor, five is intermediate, and nine is very good, respectively for resistance to root lodging). There are two types of root lodging, early root lodging and late root lodging. Early root lodging occurs right before flowering. Late root lodging occurs within approximately two weeks of anticipated harvest or after pollination. Late root lodging is more problematic because of the inability of the plant to recover before harvest, which results in consequent yield losses.

Both early and late root lodging occur as a result of the interaction between the root system, the soil and the wind force pushing the plants during a storm. In moisture saturated soils, frictional forces between the root system and the soil particles are significantly reduced allowing the root to rotate when a lateral force is applied to the stalks. This rotation is in the direction of the force vector after the consequent lodging.

As those skilled in agricultural arts know, nearly every part of the corn plant has a use. Corn is used as human food, livestock feed, and as a raw material in many industries. The food uses of corn, in addition to human consumption of corn kernels, include products of both dry- and wet-milling industries. The principal products of corn dry milling are grits, meal and flour, while the corn wet-milling industry provides starch, syrups, and dextrose for food use. Corn oil is recovered from corn germ, which is a by-product of both dry- and wet-milling industries.

Corn is also used extensively as livestock feed primarily for beef cattle, dairy cattle, hogs, and poultry.

Industrial uses of corn are mainly from corn starch, from the wet-milling industry, and corn flour from the dry-milling industry. The industrial applications of corn starch and flour are based on its functional properties, such as, viscosity, film formation, adhesive properties, and the ability to suspend particles. Corn starch and flour have applications in both the paper and textile industries. Other industrial uses include applications in adhesives, building materials, foundry binders, laundry starches, explosives, oil-well muds, other mining applications, and for ethanol production.

Plant parts other than the grain of corn are also used in industry. Stalks and husks are made into paper and wallboard and cobs are used for fuel and to make charcoal.

Growers thus are interested in producing corn plants that have the very best grain or plant quality properties, produce the highest yield and therefore have the greatest potential for income.

An embodiment of the present invention provides a method and means of objectively measuring the susceptibility of corn plants to root lodging.

A further embodiment of the present invention provides a device which objectively measures corn plants' susceptibility to root lodging that is relatively inexpensive, easy to make and easy to use.

An embodiment of the present invention provides a method and device that can be used to test more effectively a hybrid's susceptibility to root lodging earlier in the product development cycle of a new hybrid than existing standard methods. Moving the testing for this trait much earlier in the development cycle allows for selection and advancement of the more desirable lines more easily, and at a point in the process when seeds of a new hybrid are relatively limited in numbers, which poses constraints with traditional methods that typically require more plants per hybrid for evaluation of root lodging. Also, traditional methods of scoring for such lodging depend on growing the plants in many locations in an attempt to have some locations present where naturally occurring environmental conditions occur, especially damaging winds that occur at key developmental stages. The present invention allows testing of the plants as needed, and is not dependent on the chance that a damaging wind might or might not occur, and so provides for a more reliable and resource efficient approach to testing for such traits. These embodiments as well as numerous benefits of the present invention will become apparent from the detailed description of the invention which follows hereinafter.

BRIEF SUMMARY OF THE INVENTION

A device to identify the susceptibility of corn plants to root lodging is provided. The device is used to push on a corn stalk and the force used to push on the stalk, and the vibration of the stalk during the test is recorded. As material breaks within the root mass, an accelerometer measures stalk vibration in response to the breaking events; the data is recorded to allow meaningful measurements and analysis of susceptibility of plant roots to breakage. This allows for screening of various hybrids for their susceptibility to root lodging.

DETAILED DESCRIPTION OF THE PREFERRED EMBODIMENTS

The device is used to measure the susceptibility of corn plants to root lodging. When used to push on a corn stalk, the force applied on the stalk and the vibration of the stalk due to root breakage during the test is recorded. Roots that are compromised in anchoring the plants break as a consequence of the applied lateral force. These breakage events are measured by an accelerometer, which measures stalk vibration. A software program (using Matlab, available from The Mathworks, Inc., Natick, Mass.) was written to correlate the number of breakage events in the accelerometer response and the input force to the known strength of the hybrid. It is within the skill of the art to determine the appropriate threshold of signal to noise ratio for optimal use of the device. The device can be used in early hybrid development to test for susceptibility to root lodging, before a large number of seeds are available for broad field testing, thus moving the opportunity for testing for this trait earlier in the development cycle of a new hybrid.

Figure 1:
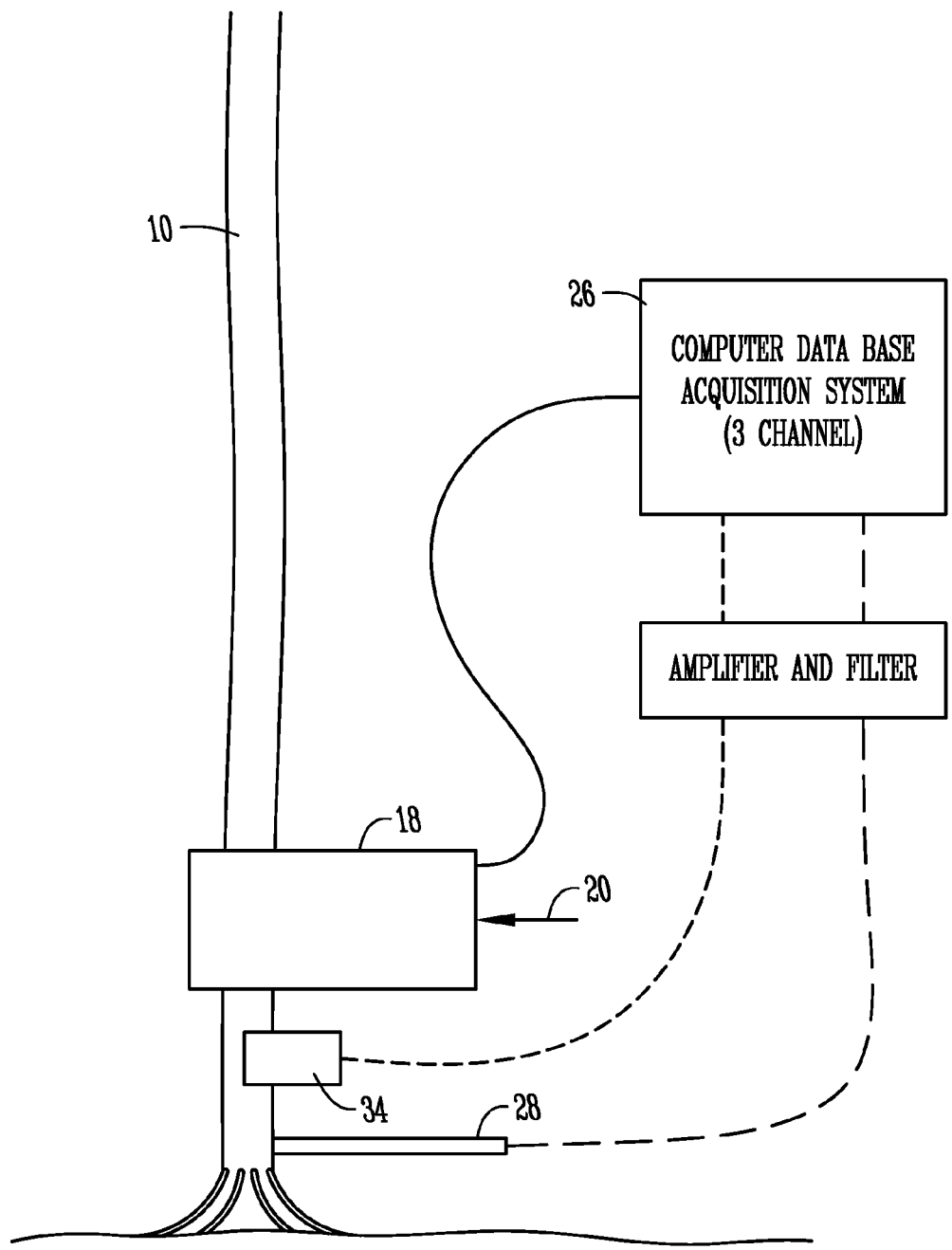
FIG. 1 is a schematic of the test setup, including the data acquisition system.

FIG. 1 is a schematic of the test setup, including the data acquisition system. A corn stalk, best illustrated in FIG. 2 at 10, has at its lower portion first, second and third internodes 12, 14 and 16, respectively. The applied test force 50 from the test device 18 is applied along the directional arrow 20 (manually as explained below), and an associated force transducer 22 records this applied force 50. The applied force 50 is preferably applied at the second or third internodes, 14 and 16, respectively.

Figure 2:
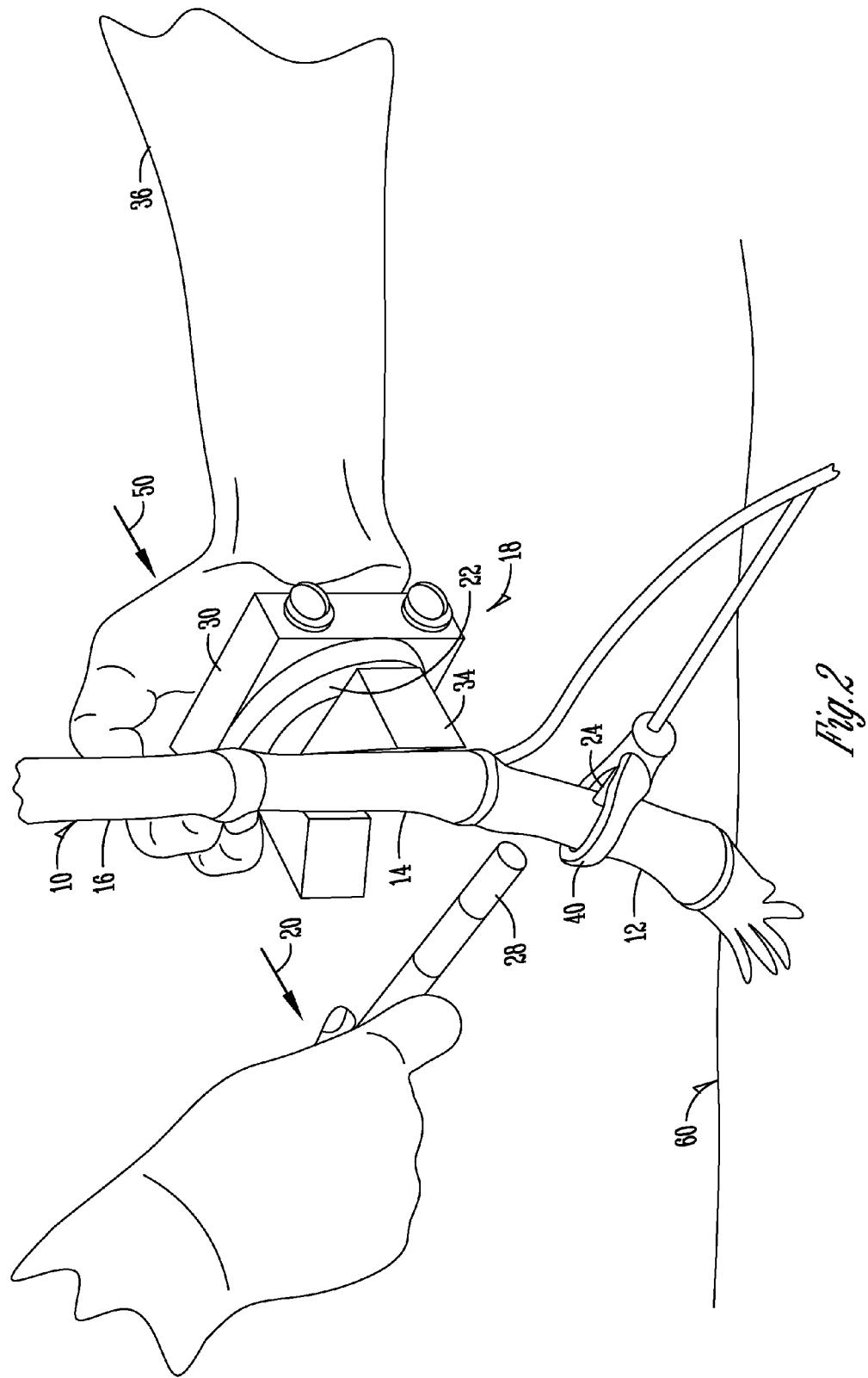
FIG. 2 is a perspective view of the components of the invention as applied to the lower portion of a corn stalk ready for measurements.

An accelerometer 24 is attached to the plant, as illustrated in FIG. 2, preferably at or above the first internode 12 and records the stalk vibrations as the root lodging occurs. The information is then stored in a computer 26 (see FIG. 1). A microphone 28 may be used to amplify the sound of root lodging which can also be stored for later analysis if desired. The microphone aspect is, however, optional, since it also picks up background noise.

Turning from the schematic of FIG. 1 to the actual device 18, as shown in FIG. 2, it should first be mentioned that initial tests were run to determine what sort of device should be used to provide consistent results. It was determined that a device designed to measure the force used to generate root lodging and the sound and stalk vibrations generated during the root lodging event would provide the desired consistent results. This measurement allows for reproducible early testing of hybrids. It was during this investigative process that it was discovered that accurate data was obtained with a handheld device, versus one that uses a mechanical drive and motor to push on the corn stalk. A device with a mechanical drive and motor to push on the stalks has its own mechanical vibrations and audible noise, both of which can interfere with obtaining accurate counts and generating consistent data. Thus an important feature for the present invention is that it is a handheld or easily portable device using manual pushing against a backing plate 30 to apply force to a plant stalk, leading to a root lodging event.

The backing plate 30 can be made from a variety of materials, including but not limited to, metals, plastics, Teflon®, nylon and wood. Specifically, an aluminum backing plate 30 is satisfactory. Force transducer 22 is mounted to the backing plate 30 so that the force 50 applied on the transducer 22 is measured. Stalk holder 34, is a plate with a V-notch in its front, and which can also be made from numerous materials as described above, is mounted, for example, with a screw to the center mounting plate of the force transducer 22. The notch portion of the V-notch of stalk holder 34 is applied against the longitudinal axis of the corn stalk to allow the force 50 to be applied perpendicular to the stalk. In this way, the user is assured force 50 is applied at the correct location. Other suitable notch shapes may be used in the present invention such as a U-notch or any variation that enables the stalk to be held in place while the test is run.

The force transducer 22 can be, but does not necessarily have to be a Loadstar AS-C-50-025 load sensor, available from Loadstar Sensors, Inc., Fremont, Calif. It is within the skill in the art to determine the suitability of other readily available force transducers. As illustrated in FIG. 2, backing plate 30, force transducer 22 and stalk holder 34 are placed at the second or third internodes, 14 and 16, respectively, as illustrated and then force 50 is applied as a human operator 36 pushes against the stalk 10.

The accelerometer 24 (one suitable example is PCB 35 2A60, available from PCB Piezotronics, Depew, N.Y.) is then positioned adjacent to corn stalk 10 at its lower end, either at the first or second internodes 12 and 14, respectively. As illustrated in FIG. 2, accelerometer 24 is affixed into the operative position by any suitable means. As illustrated here, accelerometer 24 is mounted using a velcro strip 40 circling the stalk 10 at or above the first internode 12 near the ground 60. The velcro strip 40 is then attached to the accelerometer 24 to hold the accelerometer 24 against the stalk 10. In this way, the vibration is sensed by the accelerometer 24 as the pushing force 50 causes mechanical breakage of the roots. Alternatively, accelerometer 24 may be mounted using pins or spikes (not shown) that are inserted into the stalk 10. The pins or spikes may be made of any suitable material so long as the accelerometer 24 is held against the stalk 10 such that the vibration is sensed by the accelerometer 24 as the pushing force 50 causes mechanical breakage of the roots.

As illustrated, microphone 28 may be held near to the ground 60 at the base of the stalk 10 in order to record the sound of the breaking events. However, the sound captured from the breaking root events, as opposed to the vibrations, has been found to be a less reliable predictor since the former is subject to also capturing background noise from a variety of other sources in the vicinity.

Figure 3:
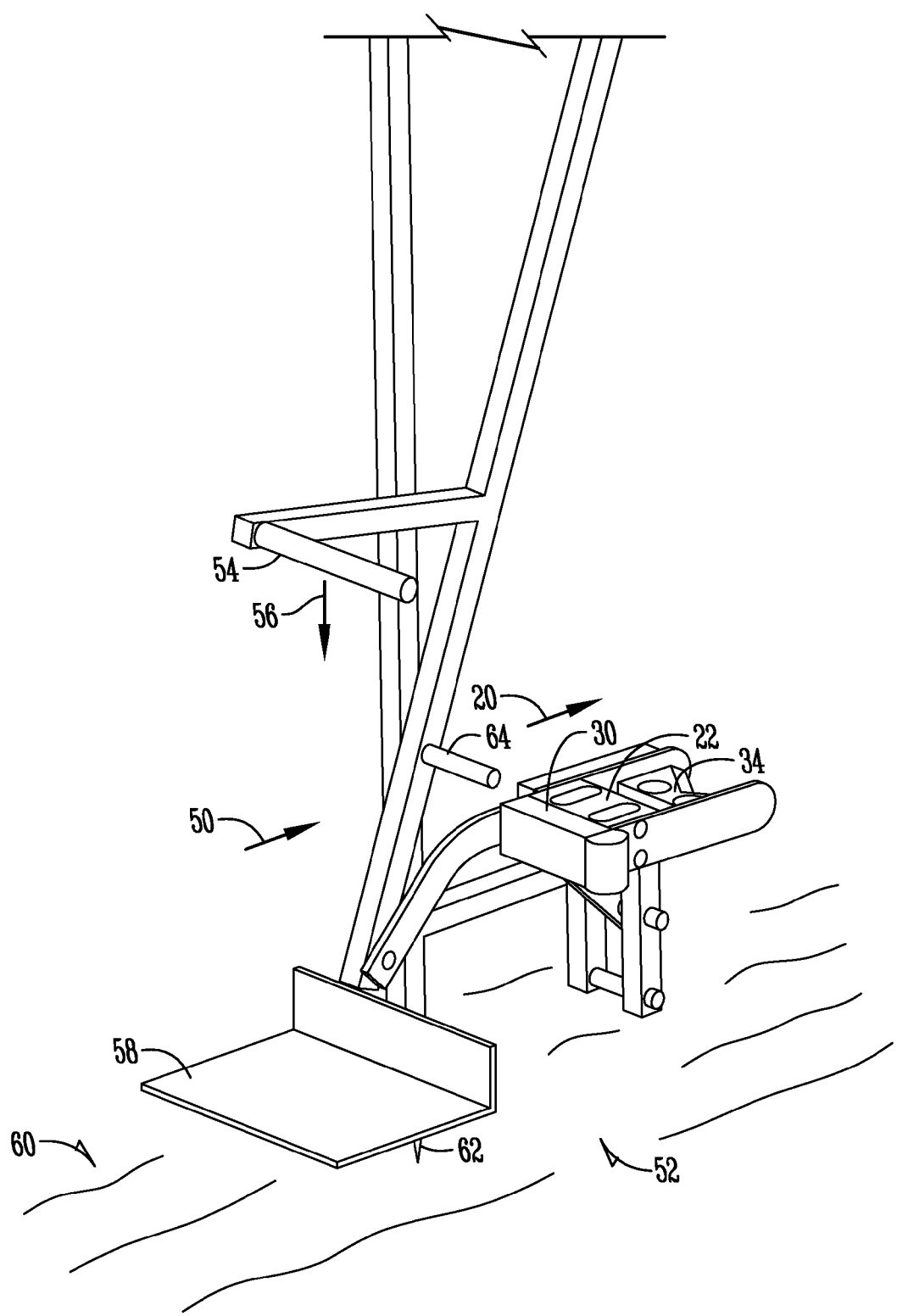
FIG. 3 is a perspective view of an additional embodiment of the invention.

A further embodiment of the present invention is shown in FIG. 3. The applied test force 50 from the test device 52 is applied along the directional arrow 20, wherein an operator (not shown) places a foot on bar 54 and pushes down along directional arrow 56 along pivot point 64, and an associated force transducer 22 records this applied force 50. Pivot point 64 may also be a cam mechanism (not shown). The applied force 50 is preferably applied at the second or third internodes, 14 and 16, respectively of the corn plant (not shown). Plate 58 of test device 52 is anchored to the ground 60 by spike 62. Plate 58 can be made from a variety of materials, including but not limited to, metals, plastics, Teflon®, nylon and wood. Specifically, an aluminum plate 58 is satisfactory. Spike 62 may be made from a variety of materials, including but not limited to, metals, plastics, Teflon®, nylon and wood. Specifically, an aluminum spike 62 is satisfactory. Spike 62 is securely fastened to the ground 60 to prevent movement of plate 58 of test device 52.

Figure 4:
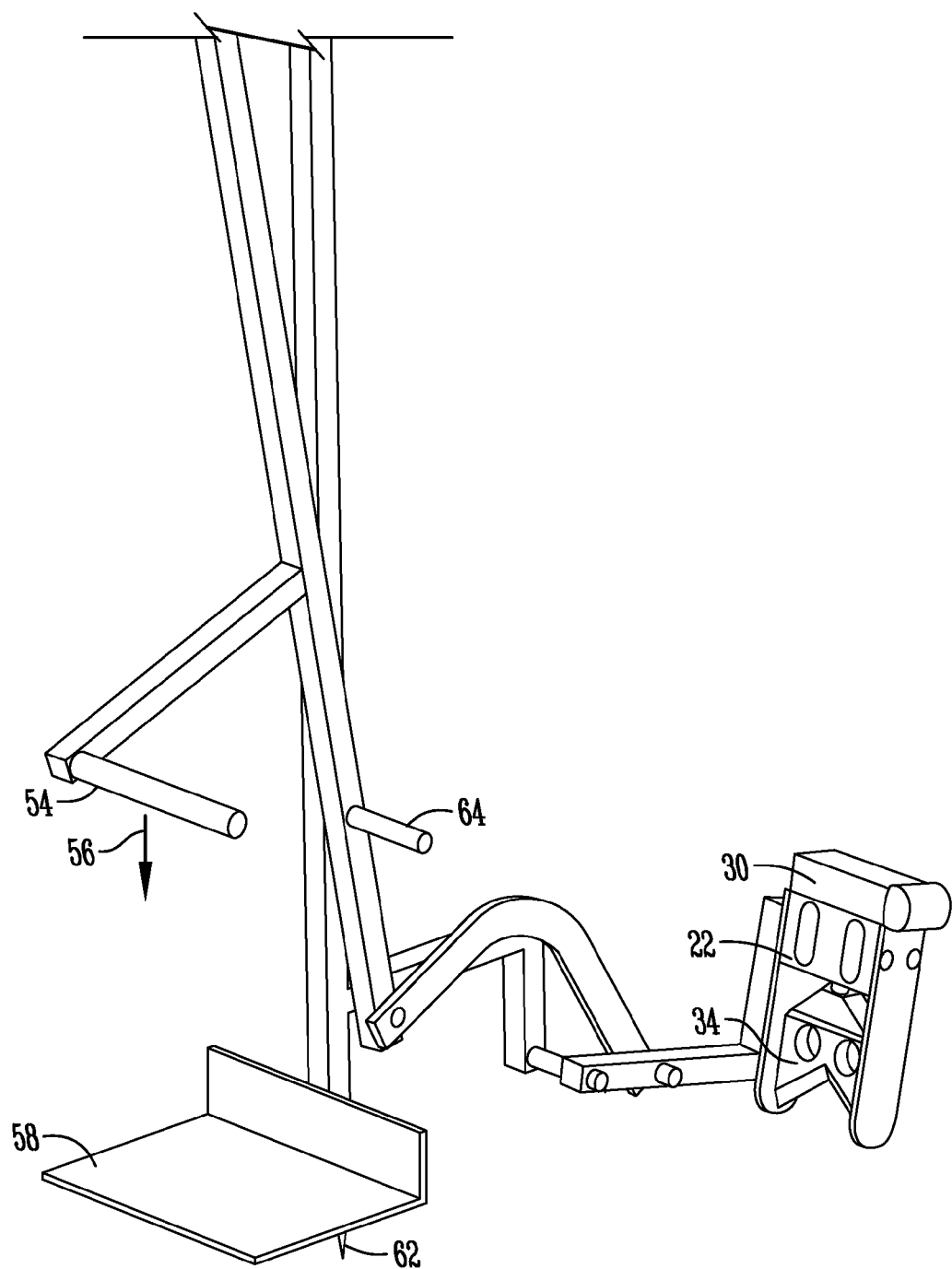
FIG. 4 is a perspective view of the embodiment of FIG. 3 in an engaged position.
Figure 5:
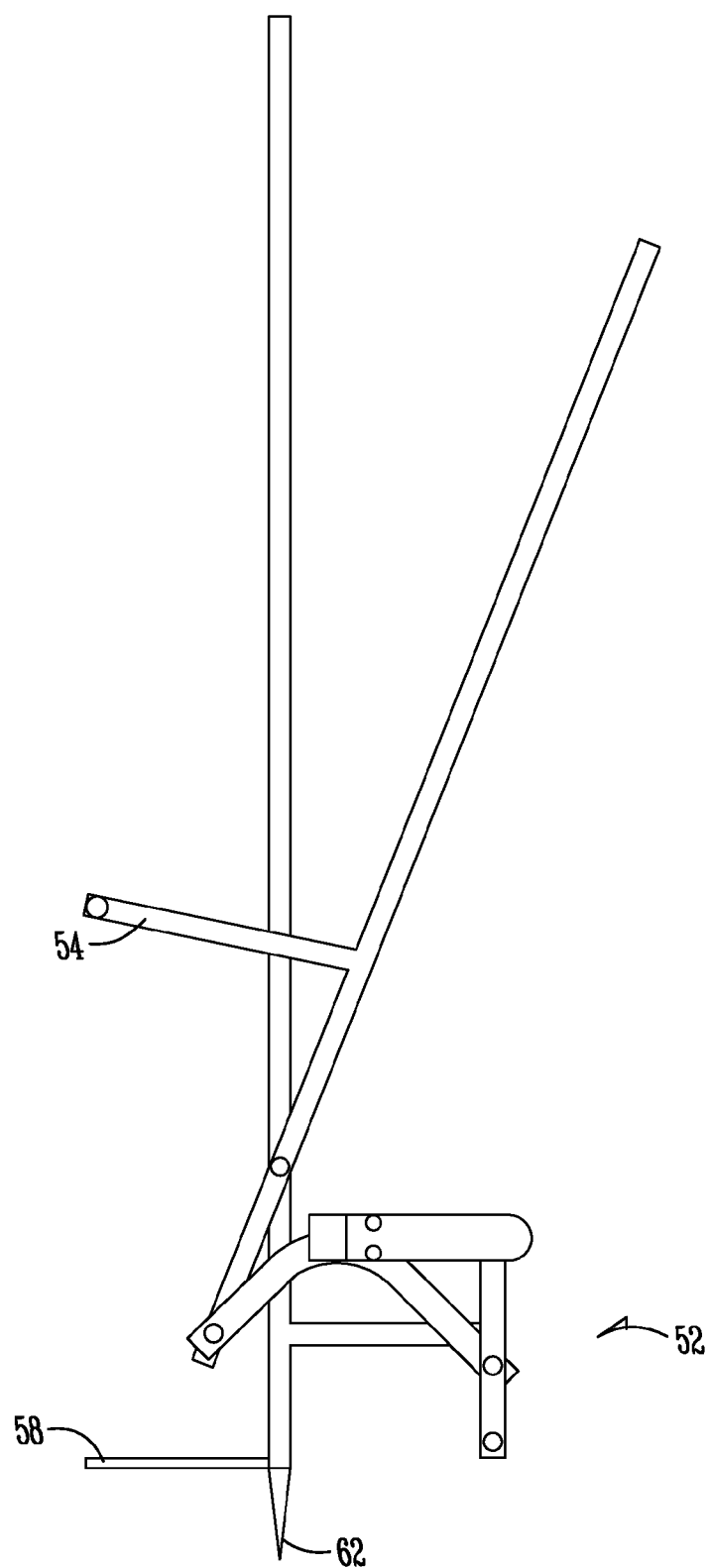
FIG. 5 is a side view of the embodiment of FIG. 3.

An accelerometer 24 is attached to the plant, as illustrated in FIG. 2, and as previously described. The backing plate 30 can be made from a variety of materials, including but not limited to, metals, plastics, Teflon®, nylon and wood. Specifically, an aluminum backing plate 30 is satisfactory. Force transducer 22 is mounted to the backing plate 30 so that the force 50 applied on the transducer 22 is measured. Stalk holder 34, which is a plate with a V-notch in its front, and which can also be made from numerous materials as described above, is mounted, for example, with a screw to the center mounting plate of the force transducer 22. The notch portion of the V-notch of stalk holder 34 is applied against the longitudinal axis of the corn stalk to allow the force 50 to be applied perpendicular to the stalk. In this way, the user is assured force 50 is applied at the correct location. This is illustrated more fully in FIG. 4. Other suitable notch shapes may be used in the present invention such as a U-notch or any variation that enables the stalk to be held in place while the test is run.

The devices described herein can be used to push on individual plants to simulate root lodging. During the push, the force, the stalk vibration and the sound (optional) are measured. As illustrated in the schematic of FIG. 1, all were measured as time signals recorded into a personal computer based multi-channel data acquisition system. The signals were sampled at 30,000 Hz with 200,000 data points collected for each plant. The long sampling time was used to ensure that the complete lodging event was captured.

The accelerometer and the microphone signals were amplified and passed through an anti-aliasing filter with a 15,000 Hz cutoff frequency. The force transducer signal was input directly to the data acquisition system.

While the embodiments described above use a pushing force it is within the skill in the art to modify the apparatus to use a pulling force on a corn stalk. The pulling force applied to the stalk and the vibration of the stalk due to root breakage during the test is recorded as described above.

During field testing as described below in the Examples, the data acquisition system was located at the edge of the field and 150 foot long cables were used to connect the computer based data acquisition system with the power supply of the microphone, accelerometer and the force transducer. It should be noted that each device was located within approximately 3-5 feet of its power supply. The cable lengths used here did not produce any discernable loss in measuring signals. All electronic devices in the field testing were powered by one portable gas powered generator, and may be powered by other readily available appropriate sources of power.

The following examples are offered to further illustrate but not limit both the system and/or device and/or method.

Examples

In the tests, as illustrated below, the field experiment was a two-level design with three variables: a) hybrid (weak or strong roots), b) soil moisture (irrigated or dry), and c) stage of development (before pollination or near maturity). The tests were blocked relative to each variable and a total of at least 20 plants were tested for each configuration. In preparing plants for attachment of the device the plants may optionally be topped (cut-off) at the fifth internode thereby reducing background noise.

Two Pioneer hybrids were assessed, one with weak roots and one with strong roots, based on earlier testing and characterization of the hybrids. Irrigation was performed with a drip tape to maintain the soil at field capacity during the time of data collection (irrigated treatment). The developmental stage of the plants during the July testing and data collection was when tassels and silks were just beginning to shed. For the August testing, plants were tested approximately 34 days after silking. There had not been rain for at least two days prior to the testing so there was a significant difference between the non-irrigated and the irrigated conditions. The dates, times and composition of experiments for each of the field testing days was:

1. 12 Jul. 2007 (10am to 3pm)
   a. Weak root hybrid non-irrigated
   b. Weak root hybrid irrigated
   c. Strong root hybrid irrigated
   d. Strong root hybrid non-irrigated
2. 15 Aug. 2007 (9:15am to 12:30am)
   a. Weak root hybrid irrigated
   b. Strong root hybrid irrigated
   c. Strong root hybrid non-irrigated
   d. Weak root hybrid non-irrigated The applied force measurements and count data collected from the experiment were analyzed using a paired-wise Tukey analysis. The difference in the means was divided by the standard error value, the result was rounded down and then one was added to this number. This gives an estimate of the number of bins that could be used to separate different hybrids from the data of each test. Thus, if the standard error is the same as the difference of the mean then the ratio will be one and adding one to this number gives two as the number of distinct categories or bins that hybrids could be separated into. From initial results it was concluded that count data provided a greater number of bins that plants could be separated into with regards to root lodging, than applied force data (Table 1).

Table 1 shows the Tukey analysis for the event counts from both experiments. The analysis was applied separately to the early and late data. The results from the non-irrigated treatment were omitted since most treated plants broke at the base of the stalk while pushing them. The soil resistance to the rotation of the root mass under non-irrigated soil conditions caused stalk lodging which confounded the results. The P values are less than 0.05 for all except the applied force in the early test. Thus for the event count in the early and late tests and the force for the late test, the strong and weak hybrids can be distinguished. In the case of the event count, there are at least three bins that the hybrids could be separated into, however, for the late data, the force could only be used to separate the hybrids into two bins and would only apply to the late data.

TABLE 1

Summary of Tukey Analysis of Event Count and Applied Force (N) Data - Separate Analysis for Early and Late Root Lodging Events (0.005 threshold - irrigated)

|  |  | Difference of Means | SE of Difference | P Value | # bins of SE Difference in Mean Difference |
|---|---|---|---|---|---|
| Event Count Data | Early | 110.3 | 38.47 | 0.0066 | 3 |
|  | Late | 370.8 | 99.03 | 0.0006 | 4 |
| Applied Force Data | Early | 4.27 | 6.95 | 0.302 | 1 |
|  | Late | 17.00 | 9.04 | 0.068 | 2 |

Table 2 shows the Tukey analysis for the early and late data combined. In this case, the analysis compared the effect of time (early and late) and also the effect of the hybrid (weak and strong). For both the force and event count, the P values are below a 0.05 threshold. Analysis of the combined data shows that using event count can provide at least 10 bins for separating the results, whereas using the applied force data allows for only three bins.

TABLE 2

Summary of Tukey Analysis of Event Count and Applied Force (N) Data - Separate Analysis for Early and Late Root Lodging Events (0.005 threshold - irrigated)

|  |  | Difference of Means | SE of Difference | P Value | # bins of SE Difference in Mean Difference |
|---|---|---|---|---|---|
| Event Count Data | Early/Late | −877.6 | 51.96 | 0.0000 | 17 |
|  | Weak/Strong | 232.4 | 23.7 | 0.0000 | 10 |
| Applied Force Data | Early/Late | −46.27 | 5.54 | 0.0000 | 9 |
|  | Weak/Strong | 11.83 | 5.66 | 0.0384 | 3 |

Based on these analyses, it appears that the event count provides greater resolution and is a more reliable approach to rate and distinguish the relative strength of hybrids for susceptibility to root lodging.

Collecting and looking at count data as an accumulated running total enabled analysis of the root breakage events over time. There appear to be two major failure modes during root lodging. At the beginning of lodging and for a period of time there are few events to be counted, then there is a point in time when the number of counts increases rapidly indicating an initial failure, followed by a plateau, then another increase, a second failure, and finally a maximum value. The data fit with known root characteristics of the hybrids used in the test.

In the irrigated results for the early testing, the strong root hybrid required a greater force for the initial failure modes. However, for the second failure mode, the weak root hybrid required a larger average force. In the late testing, the force needed to lodge the strong root hybrid was consistently higher. Thus it was possible to use the device described herein to distinguish between known hybrids having strong or weak roots for their susceptibility to root lodging.

From this information it can be seen that a unique handheld device reliable in predicting important mechanical properties of corn roots has been designed and developed which enables the collection of meaningful and important data to facilitate corn breeding and product development processes.

What is claimed is:

1. A device for measuring plant stalk and root strength, comprising:
    a stalk holder to apply force to a plant stalk;
    a transducer operably linked to the stalk holder to output a voltage signal related to force applied by the stalk holder;
    an accelerometer for attachment to a plant stalk for measuring stalk vibrations as the stalk holder applies force to a plant stalk; and
    a recorder for recording the voltage output signal of said transducer and the vibration output signal of said accelerometer operably linked to each of said transducer and said accelerometer.

2. The device of claim 1 which is portable.

3. A method of measuring plant stalk and root strength, said plant having a root portion and a stalk portion, comprising:
    applying a pushing force to the lower portion of said stalk to push the stalk over;
    measuring the applied pushing force required to push the stalk over;
    measuring the vibrations in the lower portion of the stalk caused by root breakage; and
    determining the plant's root lodging properties from the measured pushing force and vibrations caused by root breakage.

4. The method of claim 3 wherein the pushing force to the lower portion of the stalk is measured in the region spanning the stalk's second and third internodes.

5. The method of claim 3 wherein the vibrations in the lower portion of the stalk are measured above the roots and below the first node of the plant.

6. The method of claim 3 wherein the plant is corn.

7. The method of claim 3 for measuring root lodging.

8. The method of claim 3 for measuring stalk lodging.

9. The device of claim 1 wherein the plant stalk is corn.

10. The device of claim 1 wherein the measuring device is for root lodging.

11. The device of claim 1 wherein the measuring device is for stalk lodging.

* * * * *